United States Patent [19]

Purzycki

[11] Patent Number: 4,913,350

[45] Date of Patent: Apr. 3, 1990

[54] AIR FRESHENER DEVICE USING EXTERNAL CAPILLARIES

[75] Inventor: Kenneth L. Purzycki, Parsippany-Troy Hills, N.J.

[73] Assignee: Givaudan Corporation, Clifton, N.J.

[21] Appl. No.: 169,664

[22] Filed: Mar. 18, 1988

[51] Int. Cl.[4] .............................................. A61L 9/00
[52] U.S. Cl. .................................................... 239/44
[58] Field of Search ...................... 239/6, 34, 44, 51.5; 261/99, 110

[56] References Cited

U.S. PATENT DOCUMENTS

| | | | |
|---|---|---|---|
| 2,350,348 | 6/1944 | Gaugler | 239/44 |
| 2,529,536 | 11/1950 | Bjorksten | 239/51.5 |
| 3,211,345 | 10/1965 | Geiger | |
| 4,250,165 | 2/1981 | Foley | |
| 4,286,754 | 9/1981 | Jones | 239/44 |
| 4,304,688 | 12/1981 | Mori | |
| 4,320,873 | 3/1982 | Martens, III et al. | |
| 4,323,193 | 4/1982 | Compton et al. | 239/44 |
| 4,454,987 | 6/1984 | Mitchell | 239/44 |
| 4,609,245 | 9/1986 | Sakschek | 239/44 |

FOREIGN PATENT DOCUMENTS 2127693 4/1984 United Kingdom .

OTHER PUBLICATIONS

Promotion Brochure, dated Feb., 1986, distributed by Capillary Technology, Inc., Portsmouth, Rhode Island.

Primary Examiner—Andres Kashnikow
Assistant Examiner—Michael J. Forman
Attorney, Agent, or Firm—Robert F. Tavares; Linda A. Vag

[57] ABSTRACT

An air freshening device which allows a liquid fragrance material to be dispensed into the ambient air of a room or other designated area in a linear fashion, i.e., without distortion of the odor character and without a change in the rate of delivery. More particularly, the device comprices a reservoir, a fragrance material, and an external capillary member, wherein said external capillary member has one or more external capillary cavities, the lower portion of said capillary being in contact with the liquid fragrance material to be dispensed, and the upper portion of said capillary being exposed to the air in the room or area into which it is desired to dispense the fragrance.

12 Claims, 12 Drawing Sheets

LEMON CITRUS

ORANGE CITRUS

AIR FRESHENER DEVICE USING EXTERNAL CAPILLARIES

BACKGROUND OF THE INVENTION

1. Field of the Invention
Air freshening devices.

2. Background Art

Devices designed to dispense fragrance materials into the ambient air to impart a desirable and pleasant fragrance are well known in the art. Such devices, commonly known as air fresheners or room deodorizers, are commercially available in a variety of forms. Some of these devices are quite simple while others, which involve mechanical systems, are more complex.

Ideally, the device should be as simple as possible, require little or no maintenance and should perform in a manner that allows the fragrance material to be dispensed at a steady and controlled rate into the designated area while maintaining its odor integrity over the life span of the device. Unfortunately, nearly all of the relatively simple non-aerosol devices that are commercially available suffer from the same limitation. The odor becomes distorted over the life span of the device due to the fact that the more volatile components are removed first, leaving the less volatile components behind. This change of the composition with time eventually results in a weakening of the intensity of the fragrance since the less volatile components evaporate more slowly. It is these two problems, i.e., the weakening of intensity and distortion over the lifetime of the fragrance material, that have occupied much of the attention of those who seek to devise better air freshener devices.

Practically all devices which depend on evaporation from a surface suffer from the shortcomings mentioned above. In most of these devices, a wick, gel or porous surface simply provides a greater surface area from which the fragrance material can evaporate more quickly, but fractionation still occurs, as it would from the surface of the liquid itself, resulting in an initial burst of fragrance followed by a period of lower intensity once the more volatile components have evaporated. Due to this fractionation and perhaps a clogging of the wick and/or other evaporative surfaces, the fragrance becomes distorted and its intensity weakens perceptibly.

Various methods have been tried in an effort to overcome such problems and some have met with limited success. For example, surface active agents have been used to control the release of the fragrance, but these non-volatile substances often clog up delivery devices such as wicks and the use of such materials has not provided the desired degree of linearity of evaporation. Another method reported to be successful in minimizing distortion, involved creating a fragrance material using only components having similar volatility so that they would all evaporate at the same rate. The use of non-volatile solvents such as high boiling low-parrafin hydrocarbons has also been reported to slow down the initial burst of fragrance caused by the more volatile components. (See U.S. Pat. Nos. 2,529,536; 4,250,165; 4,304,688; 4,320,873; 4,323,193.)

The most common devices are those which, as stated above, depend on an evaporative surface and a delivery system for transferring the fragrance material to that evaporative surface. Despite the fact that most of these devices suffer from the limitation that there is distortion and a weakening of the fragrance with time, they are still very widely used inasmuch as they are simple and do provide a fragrance over a long period of time, an advantage they have over aerosol-type systems. Aerosol-type systems, while they do maintain fragrance integrity over their useful life, are useful only while they are being sprayed and, unless constantly sprayed, they lose their effectiveness in a few minutes. Each spray of the aerosol does, however, emit the same composition so that continued use does not result in distortion or decreased odor intensity. It simply is not practical, however, to use an aerosol, as a continous dispenser of fragrances.

Mechanical devices have been developed to overcome the limitations mentioned above including the problems of non-linear delivery and distortion of the air freshening material. These systems are devices which introduce a premeasured amount of the fragrance material into the ambient air at regularly timed intervals. Such devices are either electrically or battery operated. The material may be dispensed as an aerosol by a mechanical system or the device may employ fans to dispense a premeasured amount of liquid. These devices are usually complex and designed for commerical rather than home use.

None of the prior art devices fully satisfies the need for an air freshening system which is simple in design and yet can deliver an air freshening material to the ambient air over a long period of time without change in the rate of delivery, or in the odor character of the fragrance, during the life of the device.

SUMMARY OF THE INVENTION

The present invention is a novel air freshening device which allows a liquid fragrance material to be dispensed into the ambient air of a room or other designated area in a linear fashion by means of an external capillary member. More particularly the invention comprises a reservoir, a fragrance material and an external capillary member, wherein said external capillary member has one or more external capillary cavities, the lower portion of said capillary being in contact with the liquid fragrance material to be dispensed and the upper portion of said capillary being exposed to the air in the room or area into which it is desired to dispense the fragrance. Surprisingly and unexpectedly, this device releases the fragrance uniformly and linearly into the air, i.e., without distortion of the odor character, without a change in the rate of delivery, and without suffering from many of the limitations of the prior art devices which have been discussed above. Another advantage of this device is the fact that its life span depends only on the amount of fragrance material in the container and, provided that the container is large enough, the device can operate for 30 days or more without the fragrance weakening and without noticeable distortion of the fragrance.

DESCRIPTION OF THE PREFERRED EMBODIMENTS

Figure 1:
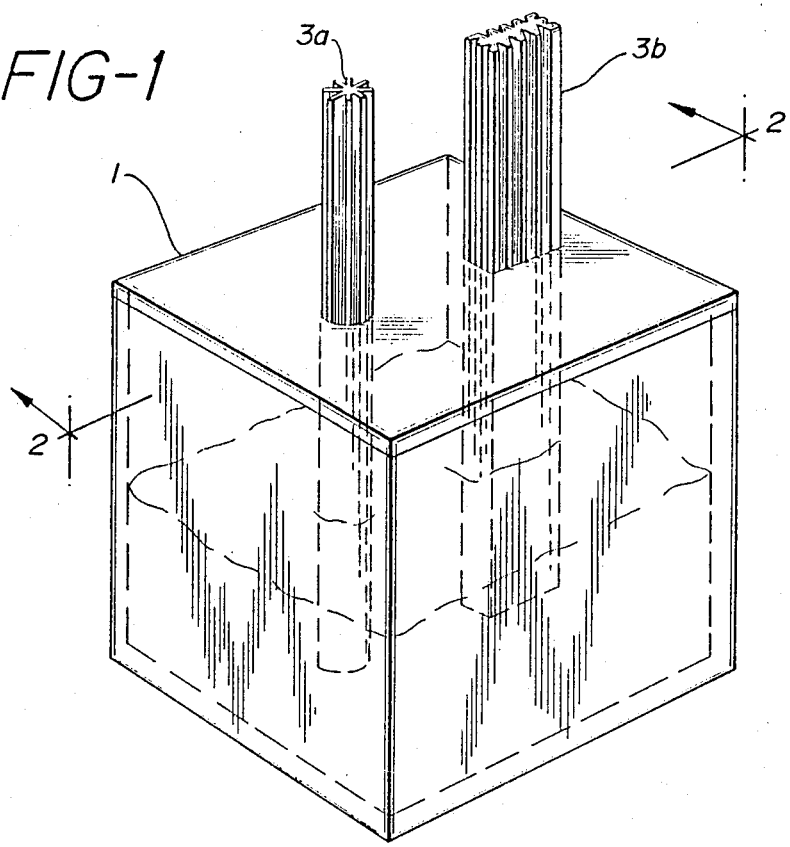
FIG. 1 shows a simple reservoir 1 with the external capillary members 3a and 3b protruding from the top.

Referring now to the drawings, wherein like reference characters refer to like parts of the Figures, the invention can be described in its simplest form as comprising an external capillary member 3, one portion of which is in contact with a liquid fragrance material 2 held in a reservoir 1 of some type and another portion of which is in contact with the air of the space into which it is desired to dispense the fragrance. In the practice of the invention, the liquid 2 rises from the reservoir 1, up the external capillary member 3 until it has reached the portion exposed to the air, and is evaporated from this portion into the air to be fragranced. The external capillary member is suitably any device having an external capillary cavity 4.

An external capillary is simply a capillary which is not completely enclosed along the sides. The capillary could simply be two plates which are close enough to allow the liquid to rise between them but which are not attached at the ends. Alternatively, an external capillary could be any device of any shape or configuration having a surface with one or more groove-like cavities having dimensions, as set forth below, which allow the liquid to rise in the cavity by capillary action from the surface of the liquid 2 to that portion of the capillary which is exposed to the air.

The purpose of the reservoir is simply to provide a container to hold the fragrance material used in the air freshening device. The design of the reservoir is not critical, but should be such that the liquid in the reservoir will be able to come in contact with the external capillary member and will be allowed to rise in the external capillary member so as to be exposed to the air to be freshened, i.e., the design should be such that the distance from the level of the liquid to the part of the external capillary that is exposed to the air does not exceed the height that the liquid is capable of rising in the capillary. Said designs are well within the scope of the art of a designer once said designer knows the criteria, as set forth below, that the design must meet.

The fragrance material can be any fragrance material suitable for imparting the desired odor. The material may be used in concentrated form or may be diluted with a suitable solvent. It is preferred to use the material in a somewhat concentrated form, i.e., with little or no solvent, since the solvent imparts no odor and would serve no useful purpose other than to provide fluidity.

Figure 3A:
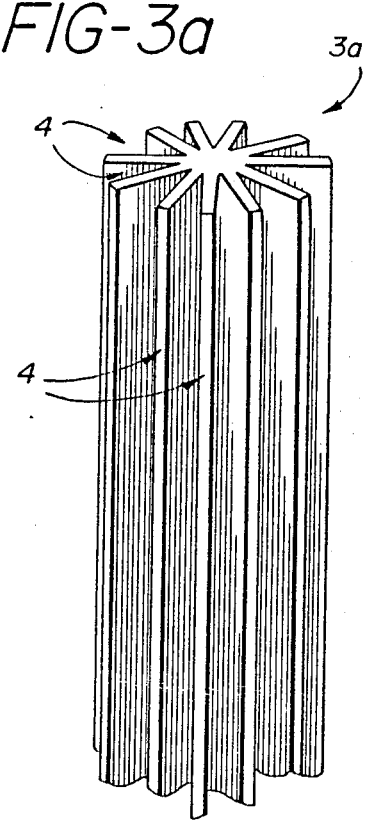
FIGS. 3a and 3b show examples of two external capillaries, one of which, 3a, is in the form of a cylindrical rod, and the other, 3b, which has a flat or rectangular box-like structure.
Figure 3B:
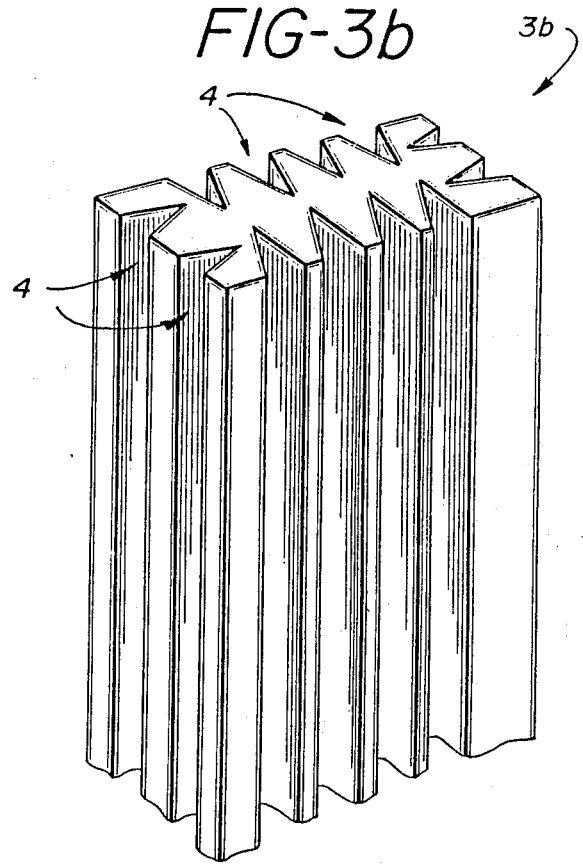
Figure 4A:
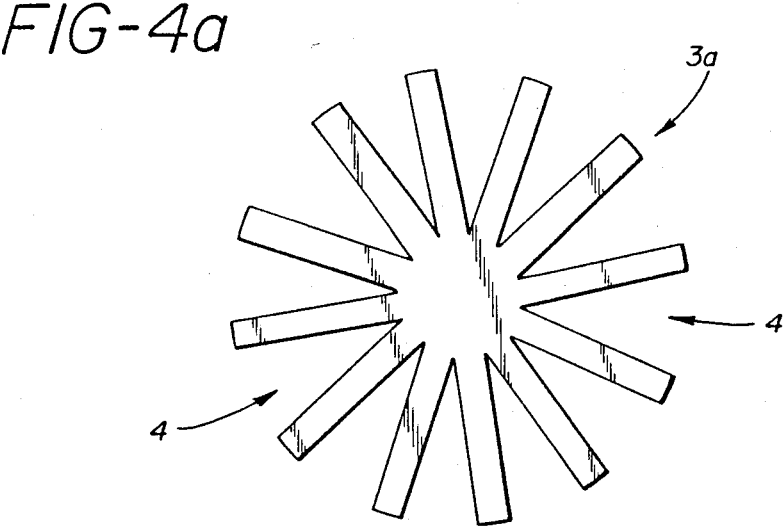
FIG. 4a shows an end view of FIG. 3a and FIG. 4b shows an end view of FIG. 3b.
Figure 4B:
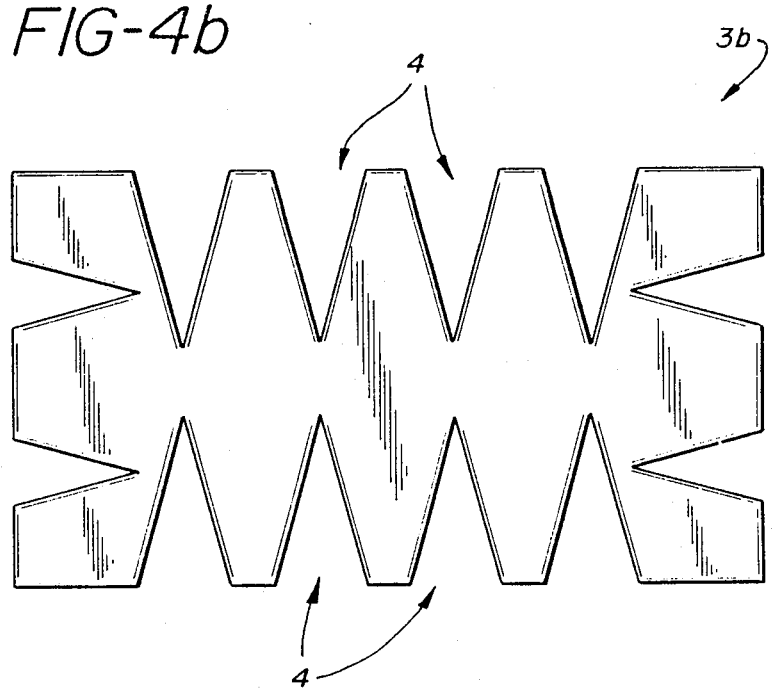

The external capillary member is preferably any device having a plurality of external capillary cavities on its surface. The shape or configuration of the external capillary member is not critical. External capillary cavities can be cut into any solid, three-dimensional figure, such as a prism, sheet, block or decorative figure which is to serve as an external capillary member. FIGS. 3 and 4 provide simple illustrations of possible external capillary members, wherein "V" shaped external capillary cavities are shown cut into cylindrical and rectangular rods.

FIGS. 3 and 4 are for illustration only, and there is no requirement that the capillary cavities be "V" shaped, or that the external capillary member be in a rod-like shape. The external capillary member can be of any shape, including that of an artistic figure. Any external capillary member will be operational so long as any external capillary cavities cut in its surface have the necessary dimensions, said necessary dimensions being discussed below.

While the "V"-shaped external capillary cavity is preferred for reasons which are given below, an external capillary cavity of any shape which fulfills the criteria set forth below, would be suitable. The practice of this invention is not dependent on either the shape of the capillary cavity or how it is made, but rather on the dimensions of the capillary cavity, as set forth below.

Figure 5:
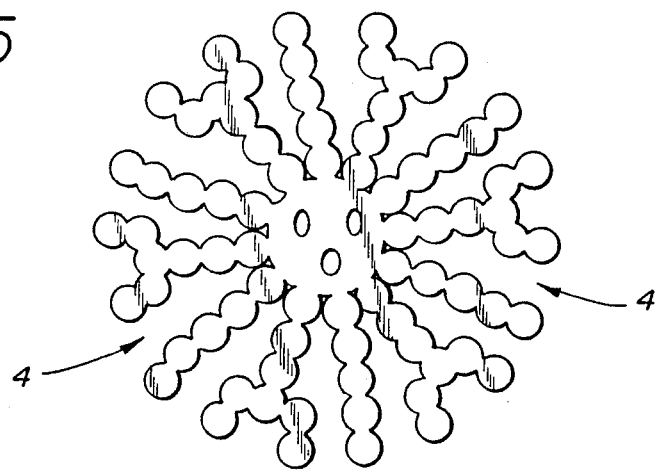
FIG. 5 shows a cross-sectional view of an extruded plastic external capillary rod of the type used in the examples.

FIG. 5 provides an accurate cross-sectional view of an external capillary member that has been manufactured by extruding an extrudable plastic through a die. The diameter or cross-sectional dimension of the external capillary is controlled by the physical restraints of the die and the speed of extrusion. The selection of such parameters are well within the skill of those knowledgeable in the art of plastic extrusions. Extruded plastic external capillary rods are commercially available from Capillary Technology, Inc., Portsmouth, Rhode Island and are suitable for use in the present invention. Because these extruded external capillary rods are commercially available, and because the extrusion process is the most economical method for making such external capillary cavitives, such extrudable external capillary rods are especially preferred in preparing the devices of this invention and reference to them are made herein to illustrate the preferred embodiments of this invention.

The rod illustrated in FIG. 5 is comprised of three central longitudinal tubes surrounded by twelve protrusions. Six of the radiating protrusions are further comprised of two additional protrusions each. The protrusions form a "V" where the apex of the "V" is connected to the central core. The open side of the "V" is on the outside surface and runs along the length of the rod. The "V" forms a cavity to conduct fluid via capillary action from a reservoir up the capillary rod. The open end of the "V" provides an evaporative surface which allows the liquid to evaporate into ambient air and act as an air freshener.

Although the cross-sectional view in FIG. 5 shows a plurality of external capillary cavities, only one is essential to deliver a fragrance material from the reservoir to the atmosphere to be fragranced. It is preferred however, to have as many external capillary cavities per rod as possible so as to more efficiently transfer the fragrance material from the reservoir to the atmosphere to be fragranced.

Figure 7:
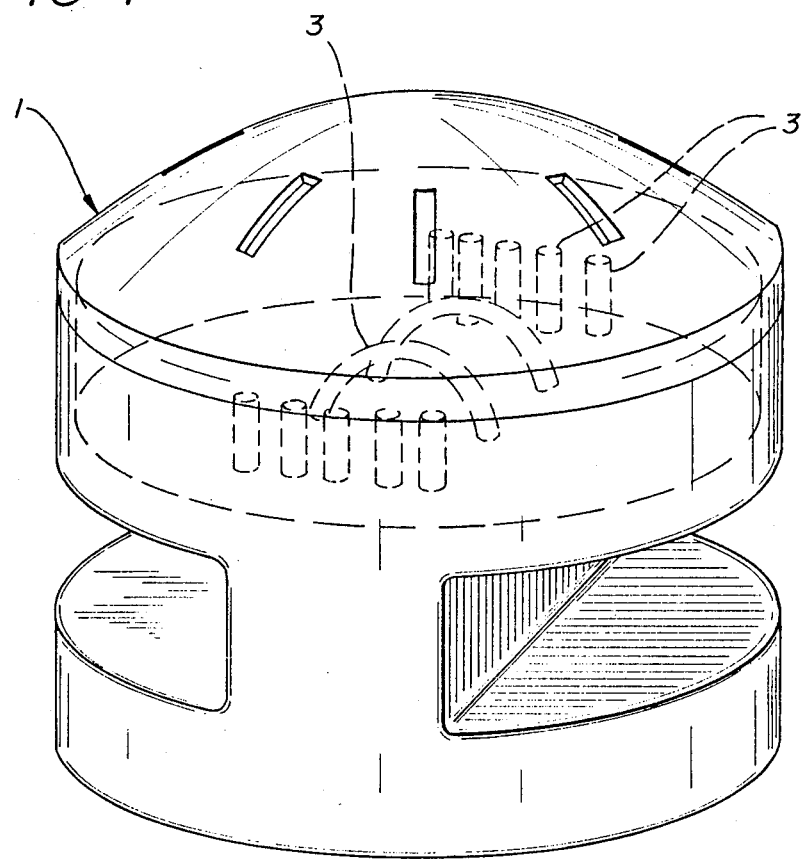
FIGS. 7 and 8 are embodiments of air freshening devices utilizing the preferred, rod-like, external capillaries, 3.
Figure 8:
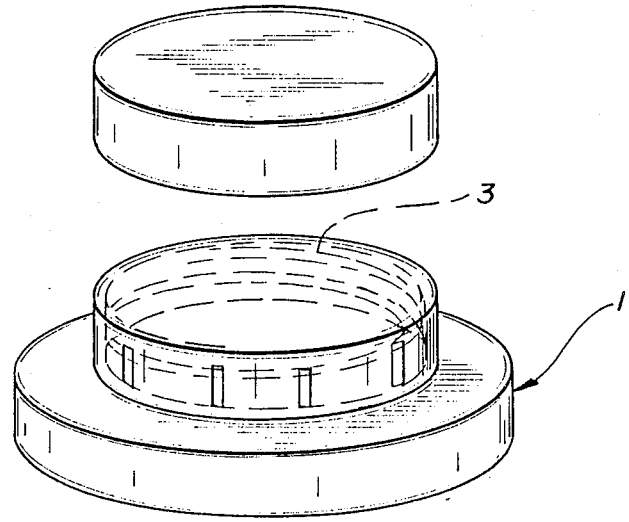

As mentioned above, capillary members are not limited to the vertical rod-like structures set forth in FIGS. 1, 2, 3 and 4 but may be any shape. FIGS. 7 and 8 illustrate the use of extruded capillary members in a more decorative setting. FIG. 7 shows both the verticle members and members which have been bent to form an arch, both ends extending into the liquid. FIG. 8 shows a single flexible external capillary member which has been coiled much as a rope would be coiled. The device could be designed where where both ends of the external capillary member were placed in the liquid and the capillary cavities would be filled from both ends. The surface of the coiled capillary device would be exposed to the ambient air, as illustrated in the drawing.

While FIGS. 7 and 8 provide illustrations using the especially preferred extruded external capillary members, other shapes and embodiments are possible as mentioned earlier. Any solid having the requisite external capillary cavity grooves, whether vertical, twisting in a spiral or thread-like manner, or existing as part of a decorative design etched on the surface of the capillary member, would be suitable as an external capillary member provided the external capillary cavity met the criteria set forth below.

As mentioned above, the critical factor in this invention is the configuration of the capillary cavity. The configuration of the capillary cavity must be such that the fragrance material will travel high enough from the surface of the liquid in the reservoir to a point at which it is exposed to the ambient air. The capillary cavity should be designed so that the liquid will rise to the desired height.

Well-established theory of capillary attraction teaches that the height (h) that a liquid will rise in a capillary will depend on a number of factors and can be calculated according to the following equation:

$$h = p\sigma(\cos \alpha)/bdg$$

wherein:
h = height that the liquid will rise in the capillary
p = perimeter of the cross section of the capillary cavity
$\sigma$ = surface-tension coefficient of the liquid
$\alpha$ = contact angle of the film with the capillary wall
b = the cross-sectional area of the cavity at the base
d = density of the liquid
g = gravity The above formula assumes that the capillary cavity is regular, i.e., the cross-sectional area (b) does not change as h changes. This equation can be used to determine whether the value of h for any particular capillary will be sufficient to carry the liquid from the reservoir to the atmosphere to be fragranced.

The only terms in the above equation that refer to the dimensions of the capillary per se are p and b (the perimeter and base area, respectively). The relationship between the height and these two dimensions of the capillary cavity can be seen more clearly by simplifying the above equation to $$h = k(p/b)$$

wherein $$k = \sigma(\cos \alpha)/dg = (\sigma/d)([\cos \alpha]/g)$$

For any particular liquid under standard conditions, k can be considered a constant since: (a) the surface tension ($\sigma$) and the density (d) depend on the liquid; (b) the gravity (g) is a constant; and (c) cos $\alpha$ can be assumed to equal 1, in most instances.

For any particular liquid, therefore, h will be directly proportional to p and inversely proportional to b, i.e., h will increase with an increase in p and/or a decrease in b.

While the ratio $[\cos \alpha]/g$ can be assumed to be constant for all liquids, the term $\sigma/d$ will vary from liquid to liquid. The results set forth in Table 5 of Example 4 show, however, that the ratio $\sigma/d$ for most fragrance materials falls within the range of $35 \pm 5$ dyne-$cm^2$/gram. In order to develop a general expression, $\sigma/d$ has been assumed to be 35 dyne-$cm^2$/gram for all fragrance materials, and the term k has been treated as a constant equal to 0.036 $cm^2$. (For purposes of this illustration, the term p, as applied to an external capillary, will be understood to mean the length of the interface, i.e. contact length, between the upper surface of the liquid and the wall of the external capillary cavity.)

Figure 2:
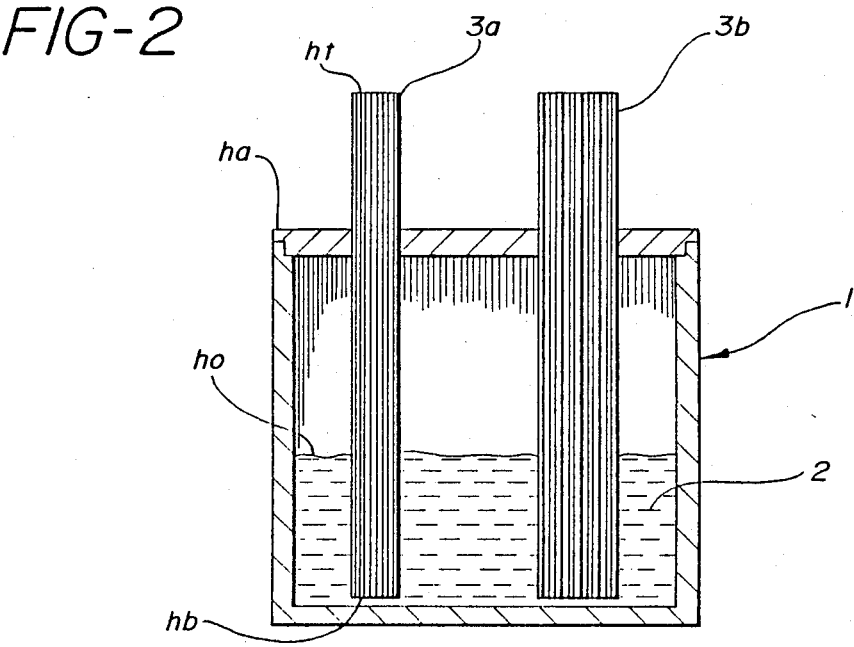
FIG. 2 is a cross-sectional view of FIG. 1 taken along line 2, and shows the external capillary members 3a and 3b having one end in contact with the liquid fragrance material 2 and the other end exposed to the ambient air.

The value of h needed will depend, for the most part, on the design of the reservoir desired. As indicated above, the size, dimensions or shape of the reservoir 1 is not critical other than to insure that the distance between the liquid surface and any part of the external capillary cavity exposed to the ambient air should not exceed the value of h as defined above. For example, consider a capillary which is divided as indicated in FIG. 2 wherein $h_b$ is the base of the capillary cavity, $h_o$ is the height of the capillary cavity which meets the surface of the liquid, $h_a$ is the lowest height on the capillary cavity where the capillary cavity is in contact with the ambient air, and $h_t$ is the top of the capillary cavity. Using these points, let $h_t - h_a$ represent the portion of the capillary which is in contact with the ambient air, let $h_o - h_b$ represent the portion of the capillary cavity in contact with the liquid in the reservoir, let $h_a - h_o$ represent the portion of the capillary which is not exposed to the liquid in the capillary nor to the ambient air, and let $h_t - h_b$ represent the total length of the capillary. Using these terms, with h being the height that the liquid will rise in the capillary cavity, the reservoir should be designed such that $h > h_a - h_o$, in order to allow the liquid to come into contact with the ambient air. It is preferred that the reservoir be designed such that $h > h_t - h_b$ since as the reservoir empties, a constant amount of material will be exposed to the ambient air over the life of the device providing a uniform and constant level of fragrance being emitted.

For any particular reservoir, therefore, the dimensions of the capillary cavity must be such that the portion $h_a - h_o$ is less than $k(p/b)$. It is preferred that the portion $h_a - h_b$ be less than $k(p/b)$ so that the fragrance will continue to be emitted into the air until the liquid level has reached the bottom of the capillary. It is especially preferred that the length $h_t - h_b$ be less than $k(p/b)$, and that $h_b$ be at the reservoir so that over the useful lifetime of the air freshening device a constant amount of fragrance will be emitted into the air and will continue to be emitted until the reservoir is empty.

As indicated above, the ratio of p/b desired for any particular device will depend on the design and size of the reservoir used and the amount of external capillary cavity to be exposed to the air. Assuming that $k=0.036$ cm$^2$, some examples of suitable p/b ratios are as follows. For example, a p/b ratio of 100 translates into an h of about 3.5 cm. A p/b ratio of 200 corresponds to an h greater than 7 cm, while a p/b ratio of 280 corresponds to an h of 10 cm. (The capillaries used in the examples were about 15 cm. This would require a p/b ratio of about 400 in order for h to be greater than $h_t - h_b$.)

While there is no practical upper limit on h or p/b, a ratio of $p/b=1,000$ corresponds to an $h > 35$ cm and there is no apparent value in designing a device which requires a p/b exceeding 1,000. For most applications, a p/b of about 550, which corresponds to an h of about 20 cm is more than sufficient. Based on the above, it is preferred to design a device wherein the p/b ratio is between 200 and 1,000, with a device requiring a p/b ratio of between 250 to 550 being especially preferred.

As indicated above, a single external capillary cavity is theoretically all that is required to deliver fragrance into the ambient air. As a practical matter, however, a plurality of capillary cavities will probably be needed to provide the desired level of fragrance to be dispersed into the room. The number of capillary cavities required would depend on a number of factors such as the size of the evaporative surface and the strength of the fragrance.

While the shape of the capillary cavity is not critical, those shapes which increase the ratio of p/b and provide a maximum evaporative surface are preferred. Example 5 illustrates how the shape of a capillary affects the value of h. For example, a square capillary will support a higher column of fragrance material than a cylindrical cavity of the same cross-sectional area, but not as high a column as a cavity in the shape of a triangle. Especially preferred is a "V" shaped external capillary cavity having the shape approaching an isosceles triangle with the base missing. (The sides need not be straight but may be irregular as shown in FIG. 5. Any irregularity which increases the ratio of p/b and does not decrease the amount of fragrance exposed to the air would be advantageous.) An isosceles triangle with the base missing, and having a small angle at the apex provides the configuration that offers the maximum advantage as to capillary capacity while also offering the maximum evaporative surface for the liquid.

The rate at which the fragrance is dispersed is directly proportional to the amount of external capillary surface exposed to the ambient air, i.e., the size and number of capillaries used and the length of each that contains said fragrance material and, is in contact with the ambient air. It is therefore well within the ability of the person of ordinary skill, knowing the average rate of dispersion per unit length of the external capillary for any particular fragrance, to be able to design a device so that the proper amount of material is dispensed per unit time. It is also well within the skill of the ordinary artisan to control the amount of air to which the external capillary is exposed by means of cap devices which can be opened via twisting or lifting means to expose only so much of the delivery system to the air, or to allow only so much air to pass by the delivery system. It should also be understood that the delivery system of the device can be augmented by fans in order to better distribute the fragrance.

At the heart of this invention is the surprising and unexpected ability of the external capillary to deliver the fragrance into the ambient air at a steady rate and without distortion. This significant absence of fractionation is attributable to the ability of the external capillary member to linearly transfer volatile materials. There is no obvious explanation as to why this happens when in most all other systems fractionation and a slowing down of the delivery occurs. The constant composition assures that the fragrance being delivered is unchanged throughout the entire period of delivery and is therefore not distorted.

All conventional fragrance materials, i.e., volatile odorous substances including essential oils, aromatic chemicals and the like, are applicable for use in the instant system. A wide variety of such materials are known to those skilled in the art of perfumery. They may comprise one or more natural materials or synthetic aromatic chemicals or a mixture of both.

ILLUSTRATION OF THE PREFERRED EMBODIMENTS

The following examples are provided herein to illustrate the preferred embodiments of this invention, and to illustrate the unique ability of the claimed device to dispense a fragrance into the ambient air without distortion and without the evaporation of the fragrance slowing down over time.

Figure 6:
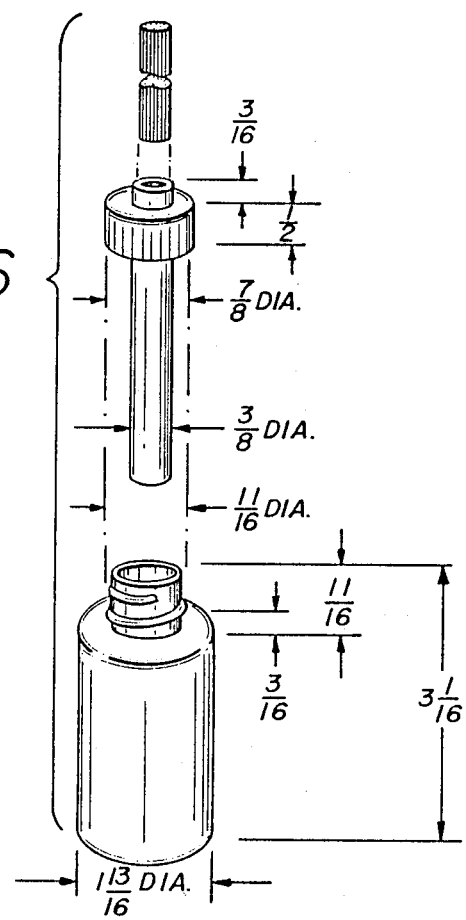
FIG. 6 is an exploded perspective view of the device that was used in the examples.

In examples 1 through 3, the loss of the volatile substance from an enclosed container was monitored over a period of time. The container used was a one ounce clear glass bottle affixed with a cap containing a glass tube, as shown in FIG. 6. (The purpose of the glass tube is to form a holding device for the external capillary rods.) The external capillary rods used in these examples were extruded plastic external capillary rods having a cross-sectional view similar to that shown in FIG. 5. The rods used had cross-sectional diameters of 1 mm, 2 mm or 3.25 mm.

Figure 11:
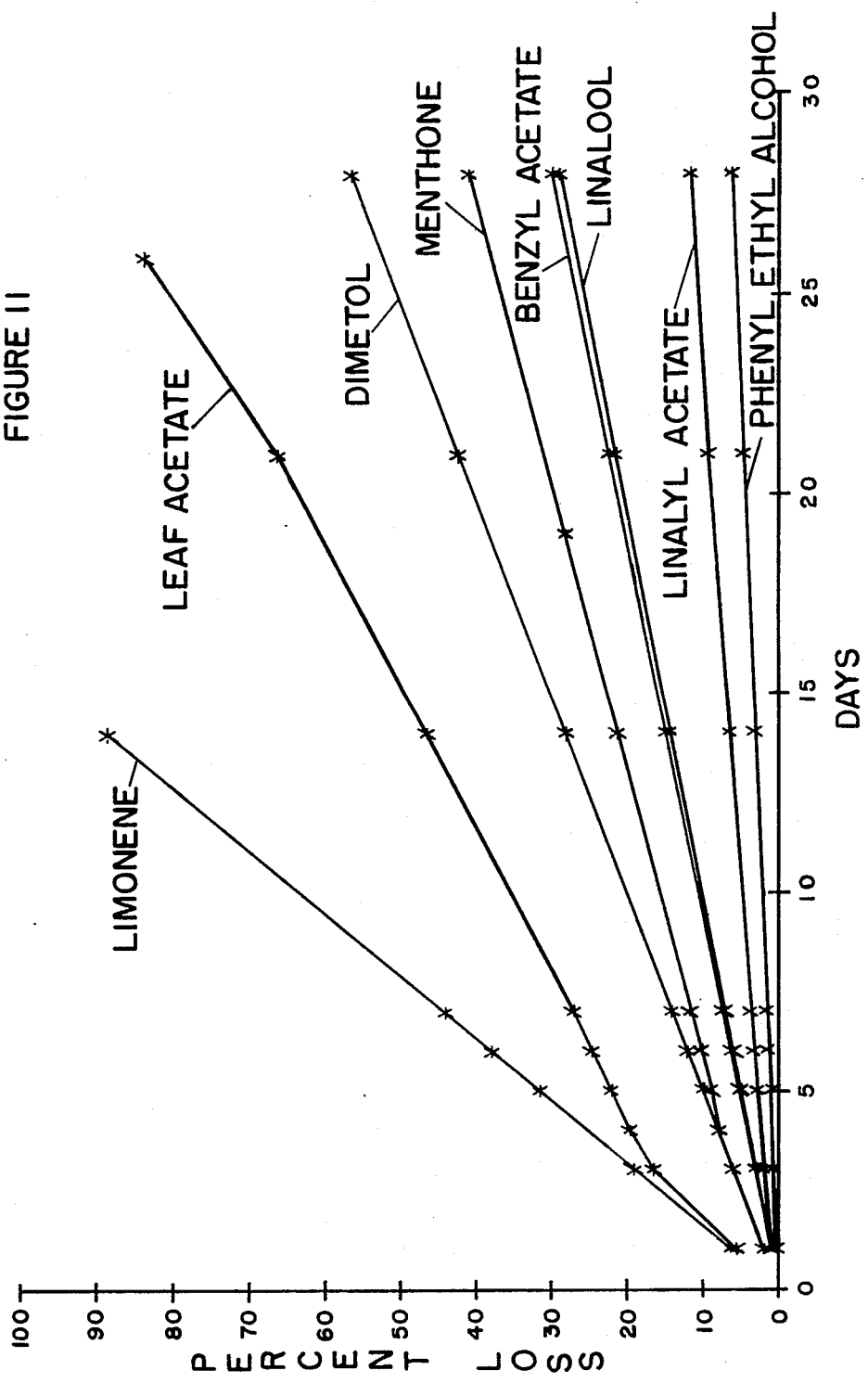
FIG. 11 shows the change in the weight loss of several common fragrance materials over time when 2 mm external capillary rods, having 1.0 inch exposed to the ambient air, are used as the external capillaries as described in Example 1A.
Figure 12:
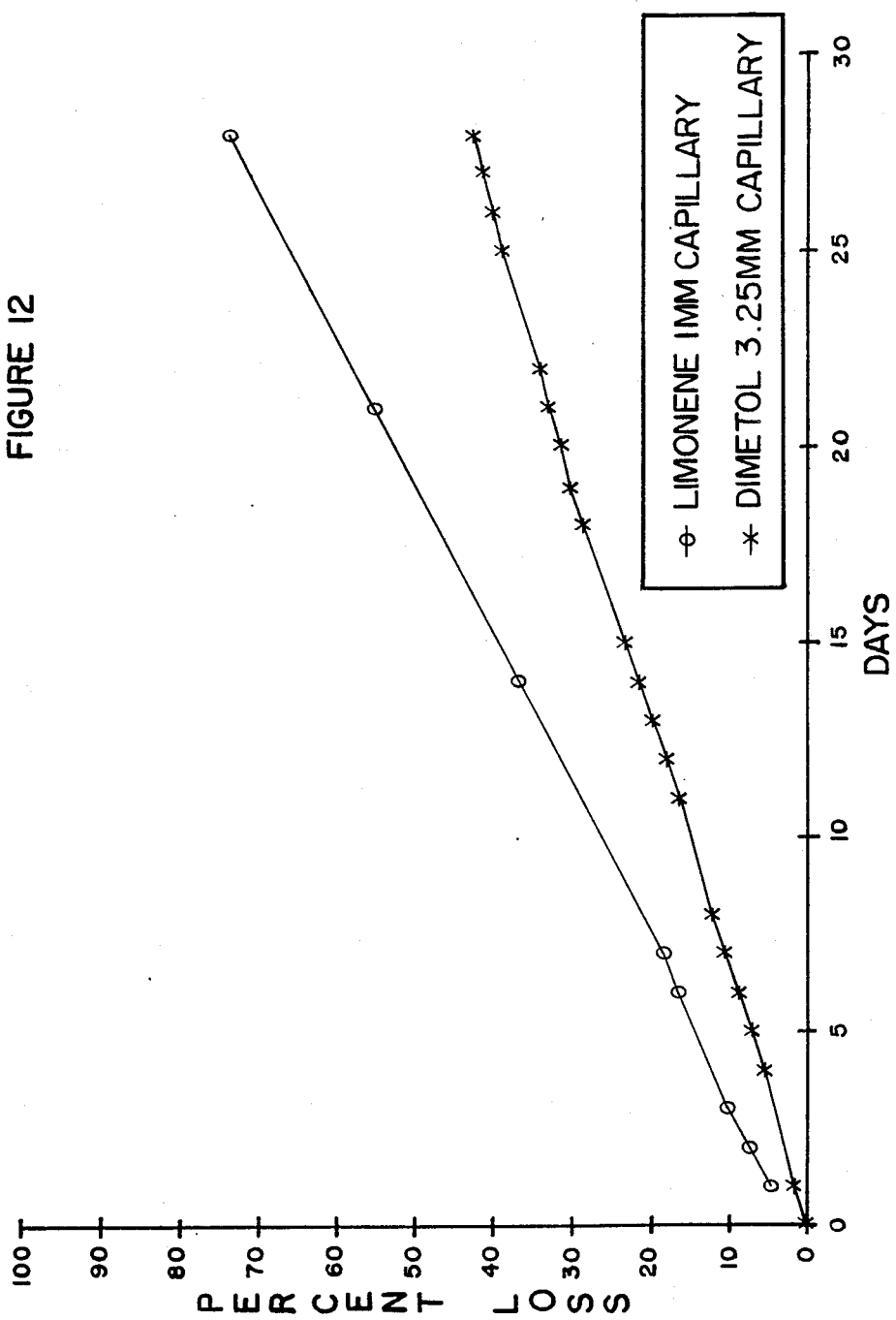
FIG. 12 shows the change in the weight loss of limonene and Dimetol ® over time using respectively 1 mm and 3.25 mm external capillary rods, each having 1.0 inch exposed to the ambient air, as described in Example 1B.

The rate of transfer of the volatile liquid from the container into the ambient air was measured by monitoring the weight-loss of the liquid in the container over a given period of time. For example, limonene, a volatile terpenoid used in the fragrance industry, is transferred linearly into the ambient air over a period of four weeks from the enclosed container shown in FIG. 6. (See Example 1 and FIGS. 11, 12 and 13.) The rate of transfer of limonene remains linear even when the rate is changed by varying the area of the external capillary rods exposed to the ambient air, i.e., exposing one inch of the rods results in a linear transfer of the material which is approximately twice as fast as when only one half of an inch of the rods are exposed. (See Example 1C.)

The lack of fractionation and distortion experienced with other liquid delivery systems when multi-component fragrance mixtures are used is also illustrated. For example, by monitoring the composition of the liquid system by gas-liquid chromatography (GLC), it was confirmed that the composition of simple binary, ternary and complex fragrance materials did not change over a four-week test period. (See Examples 2 and 3). This is in contrast to conventional wick systems which exhibit fast release of the low boiling components followed by the slow release of the medium and high boiling components.

Examples 4 and 5 are provided herein to illustrate how how varying certain parameters in the design of the capillary cavity of the external capillary member affect the height to which the fragrance material will rise in the capillary. Example 5 illustrates that the preferred shape of a capillary cavity is the V-shape of an isoseles triangle. The example further illustrates that an isoceles triangle with the base missing and having a small angle at the apex offers the maximum advantages as to capillary capacity. The data provided in the example can assist in determining a suitable length for the external capillary member of the air freshening device.

Example 4 provides the data which shows that the surface tension and density of common fragrance materials fall within a relatively narrow range. These properties of a fragrance material are two factors in determining the height to which that material will rise in a particular capillary cavity. The fact that they fall within a narrow range allows one to assume a standard value for these properties in determining the height to which any volatile fragrance material will rise in a particular capillary cavity design.

The following examples will further illustrate the preferred embodiments of this invention.

EXAMPLE 1

This example illustrates that external capillaries transfer a fragrance material linearly to the ambient air over a given period of time regardless of the size of the external capillary rod, the length of rod exposed to the ambient air, or the fragrance material being transferred. The example also illustrates that the rate at which the transfer occurs is dependent upon the area of external capillary exposed to the ambient air.

1A: This example (see FIG. 11) shows that the rate of transfer to ambient air of commonly used fragrance materials is linear. In this example, 15 grams each of limonene, Dimetol ® (Givaudan, 2,6-dimethylheptan-2-ol), linalool, benzyl acetate, phenyl ethyl alcohol, linalyl acetate, menthone and leaf acetate were respectively weighed into bottles containing fourteen 2 mm×6 inch external capillary rods with one inch exposed to the ambient atmosphere. The weight lost by each was monitored over a four-week (28 day) period and the results plotted on FIG. 11. The rate of transfer for each fragrance material was essentially linear.

1B: This example (see FIG. 12) illustrates that the rate of transfer of a fragrance material is linear regardless of the size of the capillary rod. In this example, limonene (15 grams) was weighed into a bottle containing thirty 1 mm×6 inch external capillary rods, and Dimetol ® (15 grams) was weighed into a bottle containing four 3.25 mm×4.25 inch external capillary rods. In both cases, one inch of the external capillary rod was exposed to the atmosphere. Both bottles were monitored over a four-week (28 day) period as described in Example 1A. The results are plotted on FIG. 12 which shows that both the 1 mm and 3.25 mm external capillary rods transfer common fragrance materials in a linear fashion.

1C: This example (see FIG. 13) illustrates how the rate of transfer can be controlled by varying the length of the external capillary exposed.

Limonene (15 grams) was weighed into each of two bottles. Bottle number 1 contained fourteen 2 mm×5.5 inch external capillary rods with 0.5 inch exposed to the atmosphere. Bottle number 2 contained fourteen 2 mm×6.0 inch external capillary rods with 1.0 inch exposed to the atmosphere. The weight of limonene lost from each bottle was monitored over a four week (28 day) period.

Figure 13:
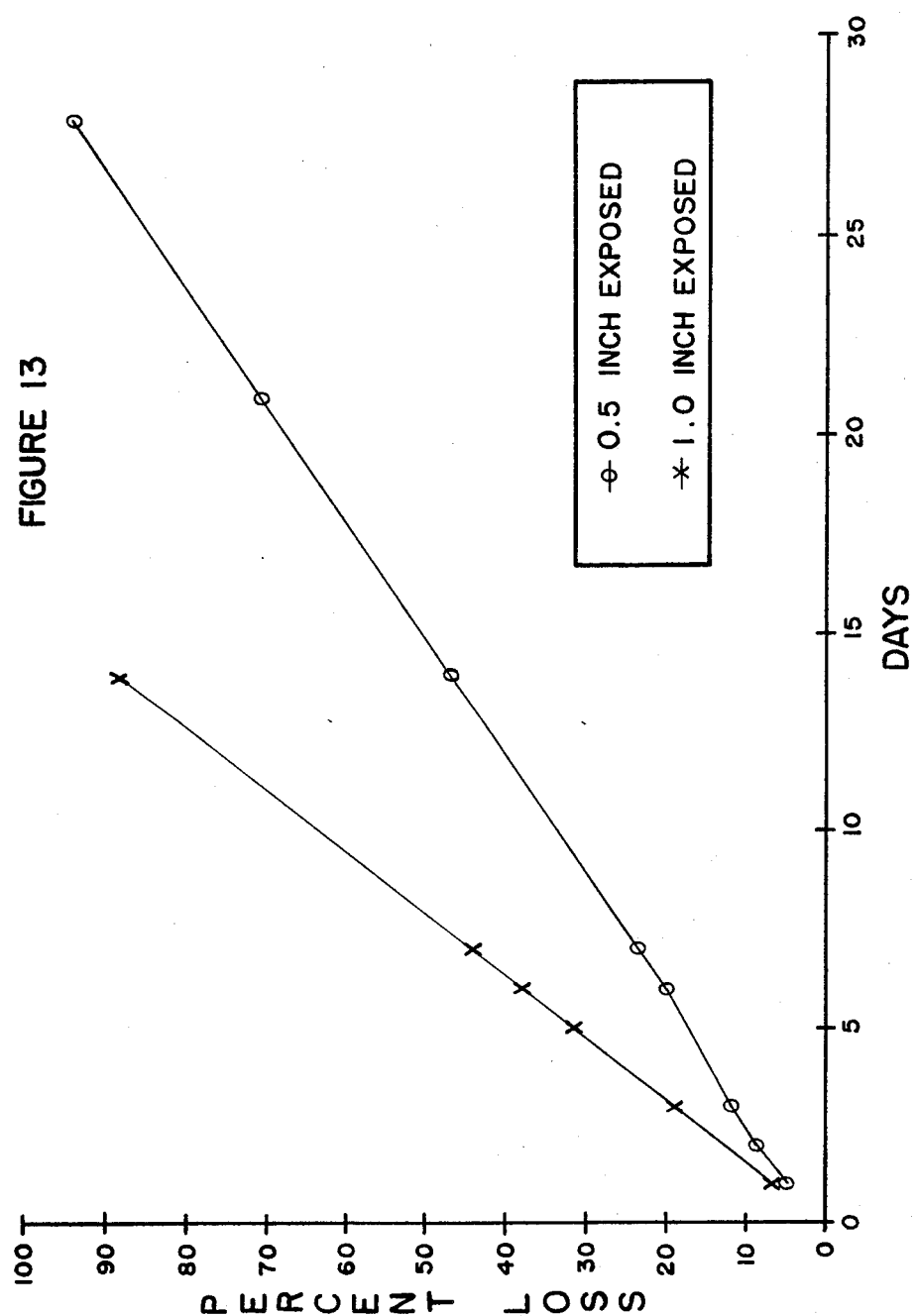
FIG. 13 shows the change in the weight loss of limonene over time when 2 mm external capillary rods, having either 0.5 inch or 1.0 inch exposed to the ambient air, are used as described in Example 1C.

The results are plotted on FIG. 13 which shows that the transfer of limonene was linear over the four week test period regardless of length of capillary exposed to the ambient air. The example also shows that the rate of transfer can be controlled by the amount of surface area exposed to the ambient air, inasmuch as evaporation from the bottle having 1 inch of capillary exposed occurred at a faster rate than from the bottle having 0.5 inch exposed.

EXAMPLE 2

This example illustrates that the rate of transfer of simple binary and ternary compositions over a given period of time is linear and that the compositions of the liquid remaining in the container is unchanged with time.

2A: Binary Composition

A 1:1 molar solution (15 grams) of limonene and Dimetol ® was placed into bottles containing fourteen 2 mm external capillary rods with one inch exposed to the ambient atmosphere. Weight loss was monitored and the composition analyzed by gas-liquid chromatography (GLC) over a 28 day period. The GLC analysis showed that the mixture remained at a constant 53/47 ratio of limonene to Dimetol ® during the test period.

Figure 14:
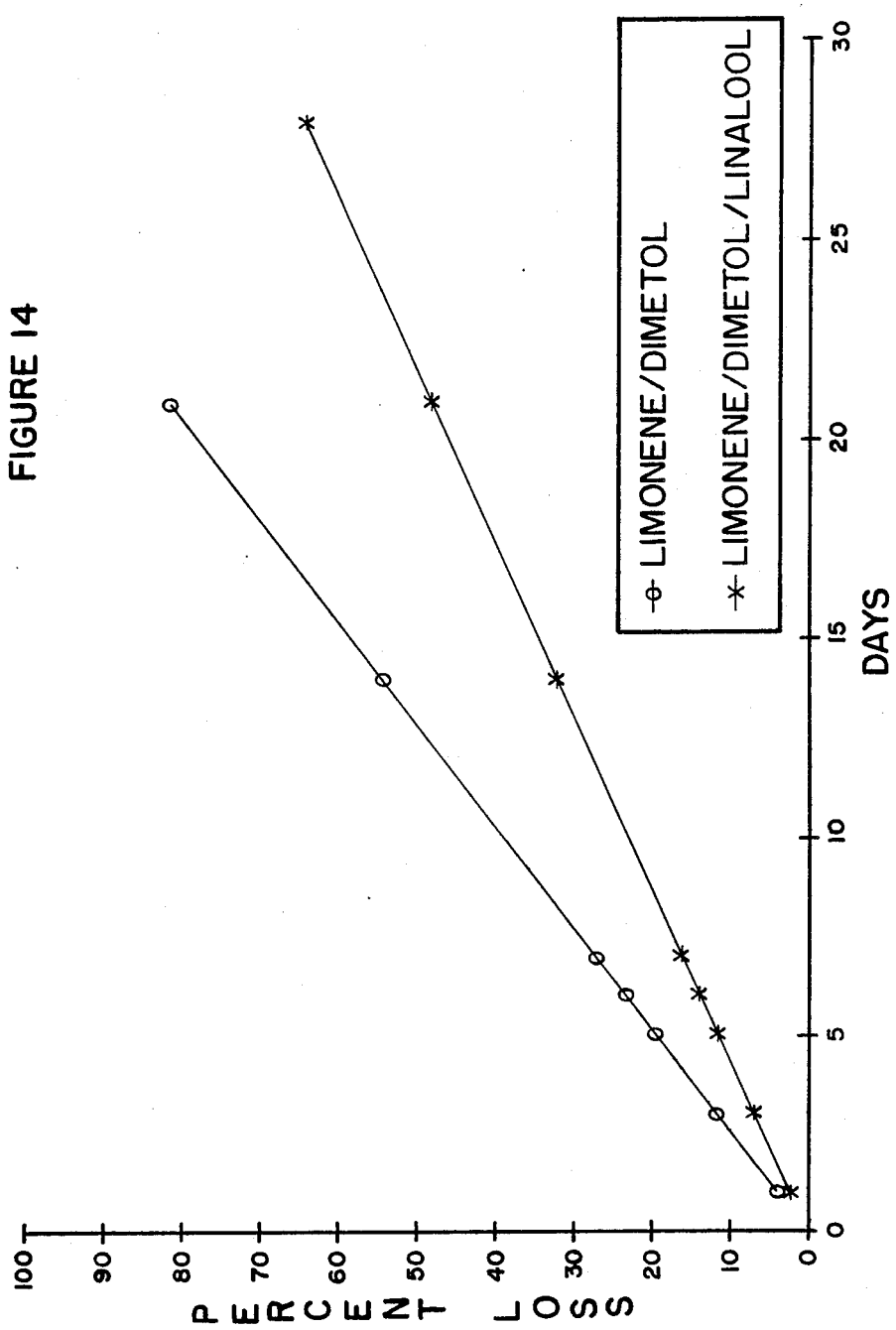
FIG. 14 shows the change in the weight loss of a 1:1 molar solution of limonene and Dimetol ® over time, and the change in the weight loss of a 1:1:1 molar solution of limonene, Dimetol ® and linalool over time when 2 mm external capillary rods, having 1.0 inch exposed to the atmosphere, are used as described in Examples 2A and 2B respectively.

The result of the weight-loss monitoring for the 1:1 mixture is plotted on FIG. 14. FIG. 14 shows that the transfer of a 1:1 molar solution, via evaporation, using external capillary rods is linear. The composition of the liquid in the container did not change with time and was identical to the initial composition. This simple binary solution shows that external capillary rods linearly transfer mixtures of volatile materials without distortion.

2B: Ternary Composition

A 1:1:1 molar solution (15 grams) of limonene, Dimetol ®, and linalool was placed into bottles containing fourteen 2 mm external capillary rods with one inch exposed to the ambient atmosphere. Weight-loss was monitored and the composition analyzed by gas-liquid chromatography (GLC) over a 28 day period. The GLC analysis showed that the mixture remained at a constant 34/30/34 ratio of limonene to Dimetol ® to linalool during the test period.

The result of the weight-loss monitoring for the 1:1:1 mixture is also plotted on FIG. 14. Graph 4 shows that the transfer of a 1:1:1 molar solution, via evaporation, using external capillary rods is linear. The composition of the liquid in the container did not change with time and was identical to the initial composition. This simple three component solution shows that external capillary rods linearly transfer volatile materials without distortion.

EXAMPLE 3

This example illustrates that complex, multi-component fragrance materials of the type commonly used in air freshening devices, perform in the same way as the simple binary and ternary compositions. A "Lemon Citrus" perfume was formulated to contain a greater proportion of less volatile components (see FIG. 9 and Table 2) while in contrast an "Orange Citrus" perfume was formulated to contain few, less volatile components (see FIG. 10 and Table 4). (Peak 1 in both perfumes is limonene.) The rate of transfer is shown to be essentially linear and the composition remains essentially undistorted throughout the test period.

3A: Lemon Citrus Perfume

The Lemon Citrus perfume (15 grams) was placed into a bottle containing fourteen 2 mm × 6 inch external capillary rods. One inch of the external capillary rods was exposed to the atmosphere. The weight loss was monitored over a four-week (28 day) period. The results are given in Table 1 and plotted on FIG. 15.

TABLE 1

| Days | Grams Lost | Percent Loss |
| --- | --- | --- |
| 1 | 0.194 | 1.29 |
| 2 | 0.296 | 1.97 |
| 3 | 0.388 | 2.59 |
| 6 | 0.672 | 4.48 |
| 7 | 0.755 | 5.03 |
| 14 | 1.219 | 8.12 |
| 21 | 1.684 | 11.22 |
| 28 | 2.179 | 14.52 |

Figure 9:
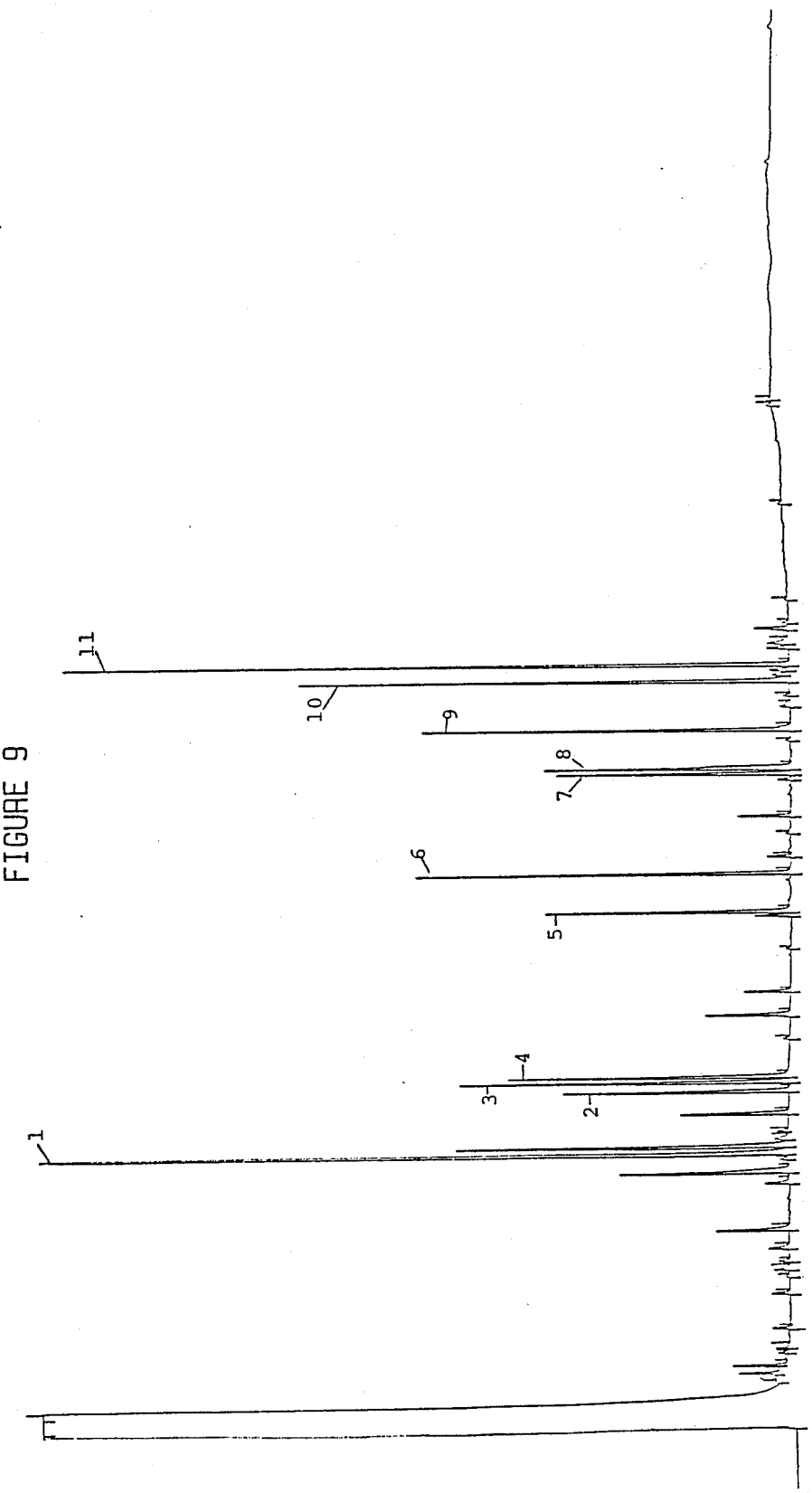
FIG. 9 shows the GLC profile of the Lemon Citrus perfume of Example 3A (SupelcoWax-10 0.25 mm i.d.×30 m fused silica capillary column, 50° to 230° C. @ 4°/min.) Components selected for monitoring are numbered 1 to 11.

The composition of Lemon Citrus perfume was monitored by gas-liquid chromatography (GLC). The chromatogram of fresh Lemon Citrus is shown in FIG. 9. Components of the perfume oil selected for monitoring over the four-week test period are labelled as peaks 1 to 11 (see FIG. 9). The results of the monitoring are given in Table 2.

TABLE 2

Component composition study of Lemon Citrus perfume

| Time (Days) | Peak Number (Percent) | | | | | | | | | | |
| --- | --- | --- | --- | --- | --- | --- | --- | --- | --- | --- | --- |
| | 1 | 2 | 3 | 4 | 5 | 6 | 7 | 8 | 9 | 10 | 11 |
| Fresh | 19.3 | 4.1 | 5.6 | 4.9 | 4.2 | 5.7 | 4.2 | 5.4 | 5.9 | 8.1 | 12.2 |
| 1 | 18.9 | 4.0 | 5.5 | 4.9 | 4.2 | 5.8 | 4.2 | 5.5 | 6.0 | 8.1 | 12.1 |
| 2 | 19.4 | 4.0 | 5.5 | 4.9 | 4.2 | 5.6 | 4.2 | 5.4 | 5.9 | 8.0 | 12.1 |
| 3 | 18.4 | 3.8 | 5.2 | 5.0 | 4.4 | 5.8 | 4.1 | 5.5 | 6.4 | 8.5 | 12.9 |
| 6 | 19.1 | 4.0 | 5.5 | 4.9 | 4.2 | 5.8 | 4.2 | 5.5 | 6.0 | 8.3 | 12.5 |
| 7 | 19.3 | 4.1 | 5.6 | 4.9 | 4.1 | 5.8 | 4.2 | 5.4 | 6.0 | 8.1 | 12.3 |
| 14 | 18.9 | 3.9 | 5.3 | 4.7 | 4.1 | 5.7 | 4.2 | 5.5 | 6.2 | 8.5 | 12.6 |
| 21 | 18.7 | 3.8 | 5.2 | 4.7 | 4.2 | 5.7 | 4.1 | 5.4 | 6.3 | 8.5 | 12.7 |
| 28 | 18.6 | 3.9 | 5.1 | 4.7 | 4.2 | 5.7 | 4.1 | 5.5 | 6.4 | 8.7 | 13.3 |

Figure 15:
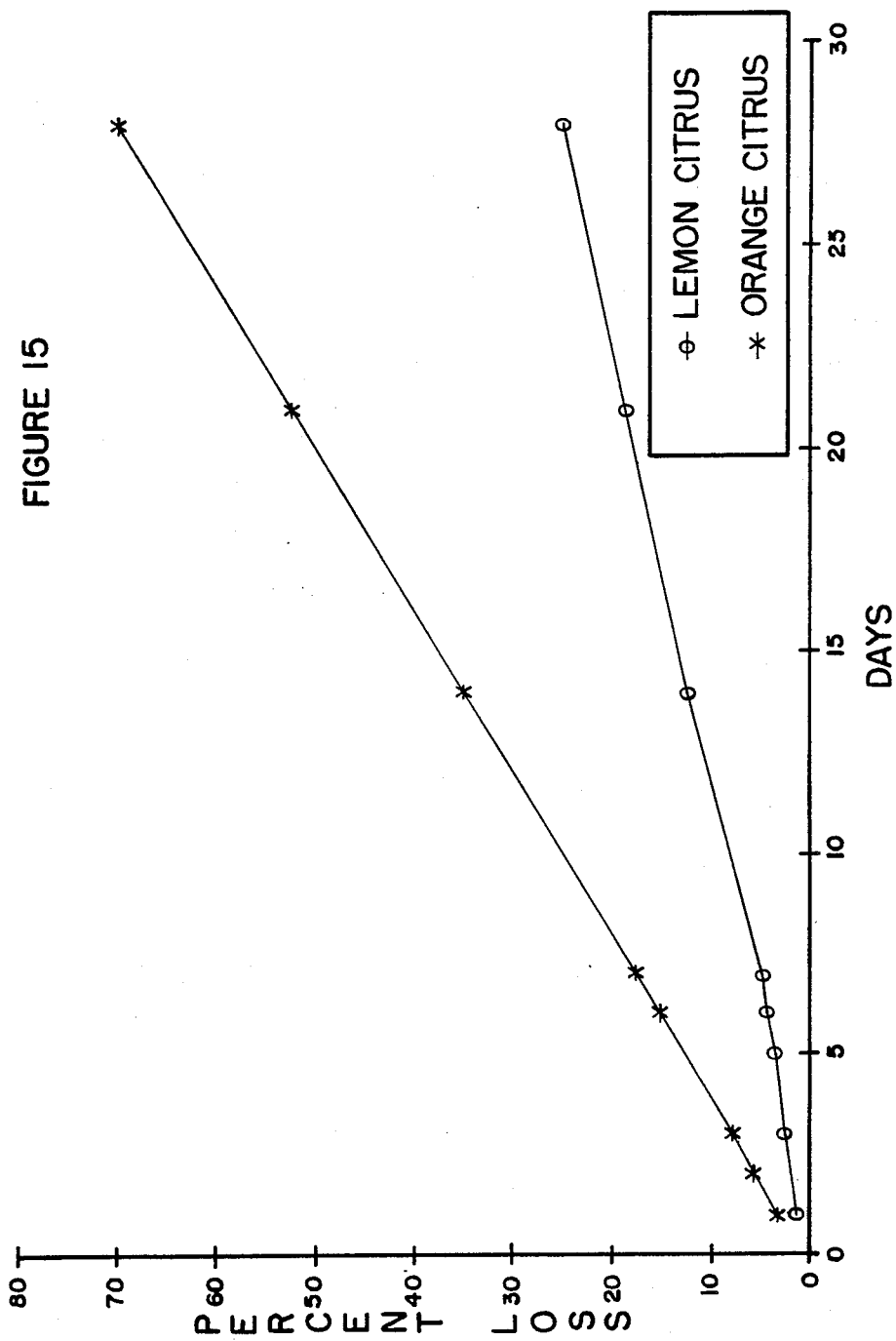
FIG. 15 shows the change in the weight loss of the Lemon Citrus perfume of FIG. 8 over time and the change in the weight loss of the Orange Citrus perfume of FIG. 9 over time when 2 mm external capillary rods, with 1.0 inch exposed to the atmosphere, are used as described in Examples 3A and 3B, respectively.

FIG. 15 shows that the transfer of Lemon Citrus perfume by external capillary rods into the ambient atmosphere is linear. Table 2 shows that the composition of the liquid perfume in the container remains consistent and is essentially similar to the initial composition.

3B: Orange Citrus Perfume

An Orange Citrus perfume (15 grams) was placed into a bottle containing fourteen 2 mm external capillary rods. One inch of the external capillary rods was exposed to the atmosphere. The weight loss was monitored over a four-week (28 day) period. The results are given in Table 3 and plotted on FIG. 15.

TABLE 3

| Days | Grams Lost | Percent Loss |
| --- | --- | --- |
| 1 | 0.494 | 3.29 |
| 2 | 0.856 | 5.70 |
| 3 | 1.179 | 7.84 |
| 6 | 2.288 | 15.22 |
| 7 | 2.644 | 17.59 |
| 14 | 4.117 | 27.39 |
| 21 | 5.455 | 36.29 |
| 28 | 6.644 | 44.20 |

Figure 10:
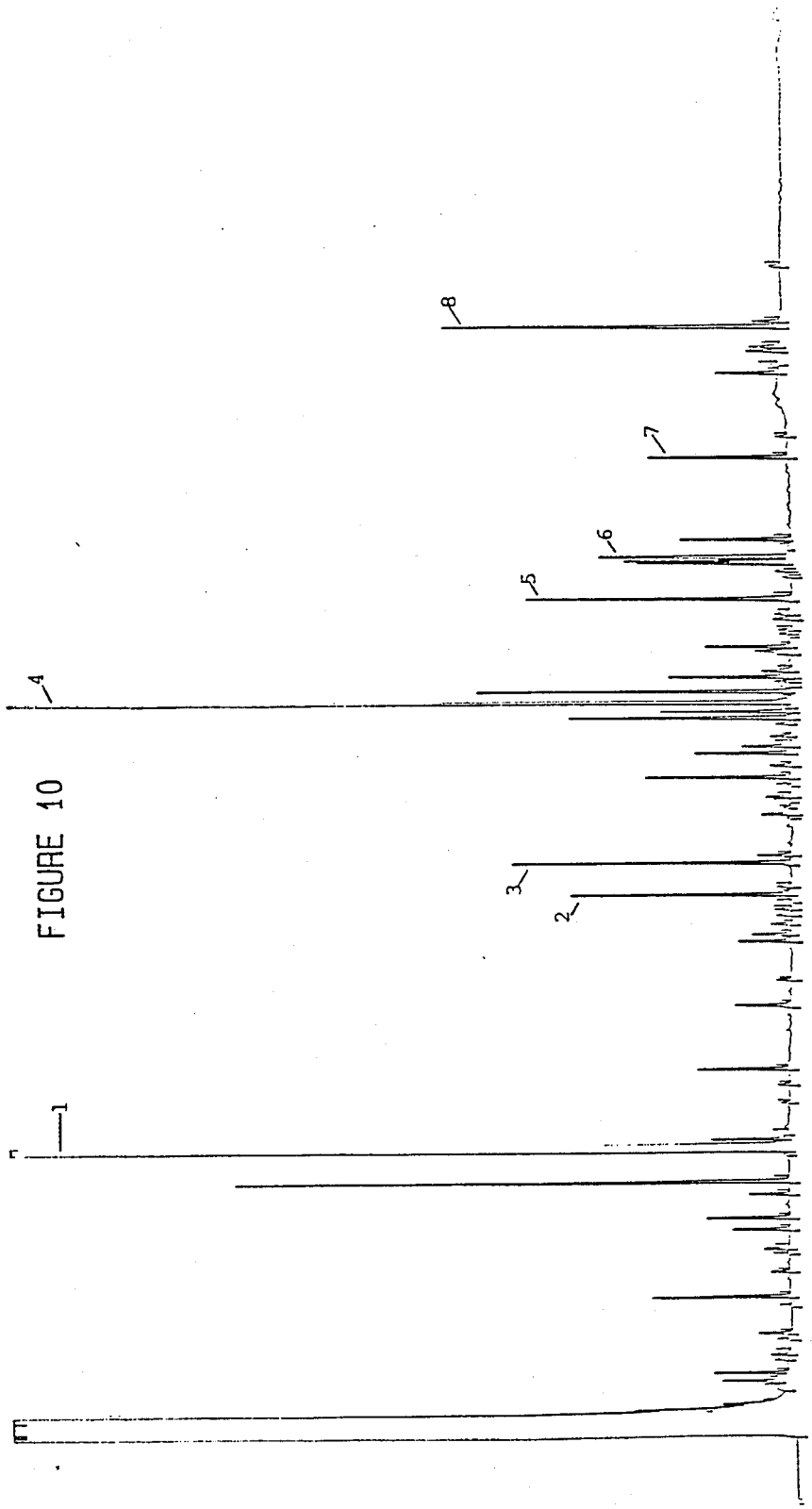
FIG. 10 shows the GLC profile of the Orange Citrus perfume of Example 3B (SupelcoWax-10 0.25 mm i.d.×30 m fused silica capillary column, 50° to 230° C. @ 4°/min.) Components selected for monitoring are numbered 1 to 8.

The composition of Orange Citrus perfume was monitored by gas-liquid chromatography (GLC). The chromatogram of fresh Orange Citrus is shown in FIG. 10. Components of the perfume oil selected for monitoring over the four-week test period labelled as peaks 1 to 8 (see FIG. 10). The results of the monitoring are given in Table 4.

TABLE 4

Component composition study of Orange Citrus perfume

| Time (Days) | Peak Number (Percent) | | | | | | | |
| --- | --- | --- | --- | --- | --- | --- | --- | --- |
| | 1 | 2 | 3 | 4 | 5 | 6 | 7 | 8 |
| Fresh | 77.9 | 0.6 | 0.7 | 6.5 | 0.8 | 0.4 | 0.2 | 1.1 |
| 1 | 81.5 | 0.7 | 0.7 | 6.7 | 0.8 | 0.4 | 0.2 | 1.3 |
| 2 | 80.7 | 0.7 | 0.8 | 6.8 | 0.8 | 0.4 | 0.2 | 1.2 |
| 3 | 80.2 | 0.7 | 0.8 | 7.1 | 0.9 | 0.5 | 0.2 | 1.2 |
| 6 | 78.5 | 0.7 | 0.9 | 7.8 | 1.0 | 0.5 | 0.2 | 1.4 |
| 7 | 78.9 | 0.7 | 0.8 | 7.6 | 0.9 | 0.5 | 0.3 | 1.4 |
| 14 | 77.8 | 0.7 | 0.8 | 8.2 | 1.0 | 0.5 | 0.3 | 1.5 |
| 21 | 74.5 | 0.7 | 0.8 | 9.1 | 1.1 | 0.5 | 0.3 | 1.6 |
| 28 | 72.8 | 0.8 | 0.9 | 10.3 | 1.3 | 0.6 | 0.3 | 2.0 |

FIG. 15 shows that the transfer of Orange Citrus perfume by external capillary rods into the ambient atmosphere is essentially linear. Table 4 shows that the composition of the liquid perfume in the container remains consistent and is essentially similar to the initial composition.

EXAMPLE 4

The densities (d) and surface tensions ($\sigma$) of a number of materials commonly used to make fragrance compositions, were measured and are recorded in Table 5. The density determinations were made using a Mettler/Parr Density Meter, Model DMA 45. The surface-tension measurements were made using Cenco-Du Nouy Model 70530 Tensiometer. The surface tension measurements reported in Table 5 are the average of three measurements. Also given in Table 5 is the ratio of the surface tension to the density, i.e., $\sigma/d$.

The list in Table 5 is not intended to be a definitive list of density and surface tension values, but rather to serve as a basis for showing that the values for the surface tension and density of those materials commonly used in fragrances fall within the relatively narrow range of $\sigma/d = 35 \pm 5$ dyne-cm$^2$/gram. The data in Table 5 provides justification for assuming that most fragrance materials will have a $\sigma/d$ ratio of about 35 dyne-cm$^2$/gram and that such a number can be used as a standard value for $\sigma/d$ in determining the height that a fragrance material will rise in a particular capillary. (See Example 5 where this assumption is applied.)

Also included in Table 5 are the Lemon Citrus perfume and the Orange Citrus perfume of Example 3 which both have a $\sigma/d$ between 34 and 35 dyne-cm$^2$/gram.

TABLE 5

| Chemical Name | d (gm/cm³) | σ (dynes/cm) | σ/d (dyne-cm²/gm) |
|---|---|---|---|
| AMYL ACETATE | 0.8760 | 25.7 | 29.338 |
| ETHANOL | 0.7900 | 23.2 | 29.367 |
| ALLYL CAPROATE | 0.8860 | 27.5 | 31.038 |
| ISOBORNYL ACETATE | 0.9900 | 30.9 | 31.212 |
| TETRAHYDROLINALOOL | 0.8300 | 26.0 | 31.325 |
| OCTAN-3-OL | 0.8200 | 25.8 | 31.463 |
| MENTHANYL ACETATE | 0.9350 | 30.1 | 32.193 |
| LINALYL ACETATE | 0.9100 | 29.4 | 32.308 |
| DIMETOL | 0.8130 | 26.4 | 32.472 |
| CEDRYL ACETATE | 1.0500 | 34.6 | 32.952 |
| DIMETHYLOCTENONE | 0.8480 | 28.0 | 33.019 |
| LEAF ACETATE | 0.8900 | 29.5 | 33.146 |
| TERPINYL ACETATE | 0.9600 | 31.9 | 33.229 |
| LINALOOL | 0.8650 | 29.1 | 33.642 |
| ALDEHYDE C-14 PURE | 0.9420 | 31.9 | 33.864 |
| LEAF ALCOHOL | 0.8580 | 29.1 | 33.916 |
| GERANYL ACETATE | 0.9050 | 30.7 | 33.923 |
| DIETHYL PTHALATE | 1.1200 | 38.1 | 34.018 |
| MENTHONE | 0.9000 | 30.7 | 34.111 |
| AMYL SALICYLATE | 1.0500 | 36.0 | 34.286 |
| METHYL OCTINE CARBONATE | 0.9140 | 31.4 | 34.354 |
| METHYL HEPTENONE | 0.8500 | 29.6 | 34.824 |
| METHYL SALICYLATE | 1.1820 | 41.2 | 34.856 |
| ALCOHOL C-8 | 0.8240 | 28.8 | 34.951 |
| ALLYL CYCLOHEXYLPROPIONATE | 0.9470 | 33.1 | 34.952 |
| CITRONELLAL | 0.8510 | 29.8 | 35.018 |
| CITRONELLOL | 0.8580 | 30.2 | 35.198 |
| EUGENOL | 1.0900 | 38.6 | 35.413 |
| GERANIOL | 0.8750 | 31.0 | 35.429 |
| LIMONENE | 0.8400 | 29.8 | 35.476 |
| ALDEHYDE C-8 | 0.8200 | 29.1 | 35.488 |
| ALDEHYDE C-16 PURE | 1.0900 | 38.7 | 35.505 |
| ALDEHYDE C-10 | 0.8250 | 29.3 | 35.515 |
| CITRONELLYL ACETATE | 0.8580 | 30.5 | 35.548 |
| ALPHA TERPINEOL | 0.9400 | 33.5 | 35.638 |
| METHYL BENZOATE | 1.0870 | 38.8 | 35.695 |
| PHENYL ETHYL ACETATE | 1.0500 | 37.6 | 35.810 |
| PARA CYMENE | 0.8200 | 29.4 | 35.854 |
| LILIAL | 0.9450 | 34.1 | 36.085 |
| ESTRAGOLE | 0.9580 | 34.6 | 36.117 |
| METHYL IONONE | 0.9280 | 33.6 | 36.207 |
| CYCLAMEN ALDEHYDE | 0.9480 | 34.8 | 36.709 |
| BENZYL ACETATE | 1.0540 | 38.7 | 36.717 |
| DIPHENYL OXIDE | 1.0730 | 40.0 | 37.279 |
| DIMETHYL BENZYL CARBINOL | 0.9760 | 36.4 | 37.295 |
| HYDROXYCITRONELLAL | 0.9200 | 34.4 | 37.391 |
| ETHYLENE BRASSYLATE | 1.0500 | 39.5 | 37.619 |
| BENZYL BENZOATE | 1.1800 | 44.4 | 37.627 |
| CITRAL | 0.8870 | 33.6 | 37.880 |
| BENZYL SALICYLATE | 1.1800 | 44.7 | 37.881 |
| AMYL CINNAMIC ALDEHYDE | 0.9650 | 36.8 | 38.135 |
| ANETHOLE | 0.9900 | 38.0 | 38.384 |
| HYDROTROPIC ALDEHYDE | 1.0100 | 39.0 | 38.614 |
| METHYL ANTHRANILATE | 1.1650 | 45.4 | 38.970 |
| BENZALDEHYDE | 1.0430 | 41.6 | 39.885 |
| BENZYL ALCOHOL | 1.0450 | 41.8 | 40.000 |
| PHENYL ETHYL ALCOHOL | 1.0300 | 42.0 | 40.777 |
| ANISIC ALDEHYDE | 1.1210 | 46.1 | 41.124 |
| CINNAMIC ALDEHYDE | 1.1100 | 46.2 | 41.622 |
| WATER | 1.0000 | 63.9 | 63.900 |
| LEMON CITRUS PERFUME | .869 | 30.3 | 34.868 |
| ORANGE CITRUS PERFUME | .856 | 29.3 | 34.229 |

EXAMPLE 5

The purpose of this example is to show how changes in the configuration of a capillary cavity affect the height (h) that a liquid will rise in a capillary cavity above the surface of that liquid in a container.

The value of h as shown previously can be determined as follows:

$$h = p\sigma(\cos \alpha)/bdg = (p/b)(\sigma/d)([\cos \alpha]/g) = k(p/b)$$

wherein:
- h = height that the liquid will rise in the capillary
- p = perimeter of the cross section of the capillary cavity
- σ = surface tension coefficient of the liquid
- α = contact angle of the film with the capillary wall
- b = the cross-sectional area of the cavity at the base
- d = density of the liquid
- g = gravity
- k = (σ/d)([cos α]/g)

In applying the above formula to calculate h, it has been assumed that cos α = 1, that the capillary cavity is regular, i.e., the cross-sectional area b does not change as h changes, and that the gravity, g, is 980.665 cm/sec². It is also helpful to note that the equation can be broken into three ratios—one of which is a function of the capillary, i.e., p/b; one of which is a function of the liquid in the capillary, i.e., σ/d; and one of which is a constant, i.e., (cos α)/g.

Based on the measurements in Example 4 and the values for g and cos α given above, σ/d will be considered to have the value 35 dyne-cm²/gram and k which equals (σ/d)([cos α]/g) will have the value 0.036 cm². Since the only parameters that are affected by the design of the capillary are p and b, the equation h = 0.036 cm² (p/b) then allows one to determine the effect that changes in the parameters defining the capillary cavity will have on the height. The equation can also be used to show that the height attained in a closed capillary should not be much greater than that attained in an open or external capillary if the parameters of the latter are properly chosen.

To illustrate how the equation h = 0.036 cm² (p/b) can be used to calculate the height to which a fragrance will rise in a closed capillary and/or an open or external capillary cavity, it is assumed that each of the capillary cavities has a "V" shape wherein the sides of the "V" are 0.05 cm each and the apex angle of the "V" is 15 degrees. If it is assumed that a side opposite to the apex angle has been added so as to create a closed capillary in the shape of an isosceles triangle, the height, h, that a fragrance would rise in such a capillary can be calculated as follows:

(a) If the equal sides of the isosceles triangle have length A, the angle between these two sides is a, and the side opposite said angle is of length B, then where A = 0.05 cm and a = 15 degrees, $$B = \sqrt{2A^2(1 - \cos a)} = 0.013 \text{ cm}$$

$$p = 2A + B = 2A + \sqrt{2A^2(1 - \cos a)} = 0.113 \text{ cm}$$

$$b = 1/2 \, A^2 \sin a = 0.000324 \text{ cm}^2$$

(b) For a closed capillary $$h = 0.036 \text{ cm}^2 \cdot (p/b) = (0.036)(0.113)/0.000324 = 12.5 \text{ cm}$$

(c) For an open capillary, i.e. the length of side B is assumed to be zero and p = 2A + B = (2)(0.05) + 0 = 0.100 cm, $$h = 0.036 \text{ cm}^2 (p/b) = (0.036)(0.100)/0.000324 = 11.1 \text{ cm}$$

As just illustrated, removal of the side B to convert a closed capillary into external capillary does not have a major effect on a capillary of the above stated dimensions.

Similar calculations were made to obtain the data in Tables 6, 7 and 8 to illustrate the affect that altering various parameters has on the height. In Table 6, the size of the apex angle is altered. (This has a dramatic affect on the height, the smaller angles producing greater heights.) In Table 7, the length of side A is varied while the angle is held constant at 15 degrees. (Again, the length of side A appears to have a significant affect on the height, although one can envision for a V-shaped capillary that only a portion of the "V" near the apex could be used effectively to act as a capillary and the height to which the liquid rises may be higher than the calculated value.) Table 8 illustrates how the shape of the capillary can affect the height.

TABLE 6

| Angle a | Length A | Length B | Area cm$^2$ | Perimeter cm | Height[a] Closed Capillary | Height[a] Open Capillary |
|---|---|---|---|---|---|---|
| 1 | .05 | 0.0009 | 0.000022 | 0.101 | 164.6 | 163.2 |
| 2 | .05 | 0.0017 | 0.000044 | 0.102 | 83.0 | 81.6 |
| 5 | .05 | 0.0044 | 0.000109 | 0.104 | 34.2 | 32.7 |
| 10 | .05 | 0.0087 | 0.000217 | 0.109 | 17.8 | 16.4 |
| 15 | .05 | 0.0131 | 0.000324 | 0.113 | 12.5 | 11.1 |
| 20 | .05 | 0.0174 | 0.000428 | 0.117 | 9.8 | 8.3 |
| 25 | .05 | 0.0216 | 0.000528 | 0.122 | 8.2 | 6.7 |
| 30 | .05 | 0.0259 | 0.000625 | 0.126 | 7.2 | 5.7 |
| 45 | .05 | 0.0383 | 0.000884 | 0.138 | 5.6 | 4.0 |
| 60 | .05 | 0.0500 | 0.001083 | 0.150 | 4.9 | 3.3 |
| 90 | .05 | 0.0707 | 0.001250 | 0.171 | 4.8 | 2.8 |

[a]The closed capillary assumes that side B is intact while the open capillary assumes that side B is removed.

TABLE 7

| Angle a | Length A | Length B | Area cm$^2$ | Perimeter cm | Height[a] Closed Capillary | Height[a] Open Capillary |
|---|---|---|---|---|---|---|
| 15 | 0.01 | 0.0026 | 0.000013 | 0.023 | 62.4 | 55.0 |
| 15 | 0.03 | 0.0078 | 0.000116 | 0.068 | 20.8 | 18.3 |
| 15 | 0.05 | 0.0131 | 0.000324 | 0.113 | 12.5 | 11.1 |
| 15 | 0.07 | 0.0183 | 0.000634 | 0.158 | 8.9 | 7.9 |
| 15 | 0.1 | 0.0261 | 0.001294 | 0.226 | 6.2 | 5.5 |
| 15 | 0.15 | 0.0392 | 0.002912 | 0.339 | 4.2 | 3.7 |
| 15 | 0.2 | 0.0522 | 0.005176 | 0.452 | 3.1 | 2.8 |
| 15 | 0.3 | 0.0783 | 0.011647 | 0.678 | 2.1 | 1.8 |
| 15 | 0.5 | 0.1305 | 0.032352 | 1.130 | 1.2 | 1.1 |

[a]The closed capillary assumes that side B is intact while the open capillary assumes that side B is removed.

TABLE 8

| Area (cm$^2$) | Circle | Triangle (Equilateral) | Square | Triangle[a] (Isosceles) |
|---|---|---|---|---|
| 0.000022 | 27.07 | 37.3 | 30.5 | 164.6 |
| 0.000044 | 19.12 | 26.4 | 21.6 | 83.0 |
| 0.000109 | 12.1 | 16.7 | 13.6 | 34.1 |
| 0.000217 | 8.6 | 11.8 | 9.7 | 17.8 |
| 0.000324 | 7.0 | 9.7 | 7.9 | 12.5 |
| 0.000428 | 6.1 | 8.4 | 6.9 | 9.8 |
| 0.000528 | 5.5 | 7.6 | 6.2 | 8.2 |
| 0.000625 | 5.0 | 7.0 | 5.7 | 7.2 |
| 0.000958 | 4.0 | 5.6 | 4.6 | 4.8 |
| 0.001175 | 3.7 | 5.1 | 4.2 | 4.7 |

[a]For the isosceles triangle, the parameters were the same as in Table 6, i.e. length A was kept constant at .05 cm and the angle was varied.

Table 8 confirms the fact that the V-shaped external capillary is the preferred shape for an external capillary. Tables 6 and 7 illustrate that the height will be greater the smaller the capillary dimensions, i.e., the smaller the apex angle a and the smaller the side A.

The values shown in the tables assume perfect shapes (triangles, V-shapes, etc.) while an actual capillary as shown in FIG. 5 has irregular sides. The irregular sides of 5 provides for a larger p and a smaller b than would be calculated for a perfect V-shape, hence the h expected should be greater than the one calculated in the examples.

I claim:

1. A device for the evaporation of a multi-component liquid into the ambient air which comprises
   (a) a container which maintains a supply of said multi-component liquid in isolation from said ambient air,
   (b) said liquid to be evaporated,
   (c) a non-porous, non-absorbing external capillary member extending from the interior of said container, through the container wall, to the outside of said container and having at least one external capillary cavity, said external capillary cavity having
      (i) a portion in contact with said multi-component liquid in the container, and
      (ii) a portion in contact with said ambient air such that the portion in contact with said liquid in the container and the portion in contact with said ambient air are connected to one another by the same external capillary cavity and, wherein the length of the portion of said external capillary that is in between the portion that is in contact with the said liquid in the container and the portion that is in contact with said ambient air into which said liquid is to be dispensed is less than the height that said liquid will rise in said capillary cavity such that the ability to evaporate the multi-component liquid in a linear fashion is maintained throughout the evaporation of the liquid.

2. The liquid evaporating device of claim 1 wherein said liquid to be evaporated is a multi-component fragrance material and said liquid evaporation device is used as an air freshner.

3. The liquid evaporating device of claim 2, wherein said external capillary cavity has:
   (a) a length $h_t - h_b$, wherein $h_t$ represents the top of the capillary cavity and is exposed to the ambient air, and $h_b$ represents the base of the capillary cavity and is exposed to the liquid in the container;
   (b) a portion $h_o - h_b$ which is exposed to the liquid in the container, wherein $h_o$ represents the top point of the capillary cavity that is exposed to the liquid in the container;
   (c) a portion $h_t - h_a$ which is exposed to the ambient air, wherein $h_a$ is the bottom point of the capillary cavity that is exposed to the ambient air,
   (d) a portion $h_a - h_o$ which represents any portion of the capillary cavity which is not exposed to the ambient air or to the liquid;
   (e) a uniform cross-sectional area equal to b; and
   (f) a contact length between the upper surface of the liquid and the wall of the capillary cavity equal to p;

wherein $h_a - h_o$ is less than 0.036 (p/b) cm.

4. The liquid evaporating device of claim 3 wherein said external capillary cavity has essentially 3 sides, one of which is partially open to the ambient air.

5. The liquid evaporating device of claim 4 wherein said external capillary cavity has greater than 50% of the third side open to the ambient air.

6. The liquid evaporating device of claim 5 wherein said external capillary cavity is essentially an isosceles triangle with the side opposite to the apex angle open to the ambient air.

7. The liquid evaporating device of claim 6 wherein the angle between the two unopened sides is less than 30 degrees.

8. The liquid evaporating device of claim 7 wherein said angle between the two unopened sides is less than 15 degrees.

9. The liquid evaporating device of claims 7 or 8, wherein $h_a - h_b$ is less than 0.036 (p/b) cm.

10. The liquid evaporating device of claims 7 or 8, wherein $h_t - h_b$ is less than 0.036 (p/b) cm.

11. The liquid evaporating device of claim 10, wherein p/b exceeds 200 cm$^{-1}$.

12. The liquid evaporating device of claim 10, wherein p/b is between 250 and 550 cm$^{-1}$.

* * * * *

UNITED STATES PATENT AND TRADEMARK OFFICE
CERTIFICATE OF CORRECTION

PATENT NO. : 4,913,350

DATED : April 3, 1990

INVENTOR(S) : Kenneth L. Purzycki

It is certified that error appears in the above-identified patent and that said Letters Patent is hereby corrected as shown below:

On the title page, in the ABSTRACT, correct "comprices" to read --comprises--.

Column 10, line 65, correct "Graph 4" to read --Figure 14--.

Signed and Sealed this

Seventh Day of January, 1992

Attest:

HARRY F. MANBECK, JR.

*Attesting Officer*  *Commissioner of Patents and Trademarks*